(12) United States Patent
Park et al.

(10) Patent No.: US 7,933,720 B2
(45) Date of Patent: Apr. 26, 2011

(54) BIOMOLECULE BONDING DETECTION APPARATUS USING RF WIRELESS ENERGY TRANSMISSION AND METHOD THEREOF

(75) Inventors: Tae-sik Park, Suwon-si (KR); Young-il Kim, Suwon-si (KR); Jung-ho Kang, Suwon-si (KR)

(73) Assignee: Samsung Electronics Co., Ltd. (KR)

( * ) Notice: Subject to any disclaimer, the term of this patent is extended or adjusted under 35 U.S.C. 154(b) by 1525 days.

(21) Appl. No.: 11/315,526

(22) Filed: Dec. 21, 2005

(65) Prior Publication Data
US 2006/0154282 A1 Jul. 13, 2006

(30) Foreign Application Priority Data

Jan. 11, 2005 (KR) .................. 10-2005-0002409

(51) Int. Cl.
*G01N 33/48* (2006.01)
*G01N 31/00* (2006.01)
*C12M 1/00* (2006.01)
(52) U.S. Cl. .................. 702/19; 702/22; 435/283.1
(58) Field of Classification Search .................. None
See application file for complete search history.

(56) References Cited

U.S. PATENT DOCUMENTS

| 5,294,889 A | 3/1994 | Heep et al. ............ 324/678 |
| 2002/0140440 A1 | 10/2002 | Haase ............ 324/678 |
| 2002/0196009 A1* | 12/2002 | Sewald ............ 324/76.51 |
| 2004/0086292 A1 | 5/2004 | Kamimura | |

FOREIGN PATENT DOCUMENTS

WO  WO 03/102602 A2  12/2003

OTHER PUBLICATIONS

European Search Report; Application No. EP05 02 8747; Date: May 23, 2006.

* cited by examiner

*Primary Examiner* — Eric S Dejong
(74) *Attorney, Agent, or Firm* — Cantor Colburn LLP

(57) ABSTRACT

An apparatus for detecting a biomolecule bonding using a radio frequency (RF) wireless energy transmission and a method thereof are disclosed. The method includes transmitting RF energy to a sensor module having one or more probe biomolecules immobilized thereon, and determining a first energy charging time of the sensor module, the first energy charging time representing the amount of time for the sensor to be completely charged by the transmitted RF energy, prior to mixing of the one or more probe biomolecules with one or more target sample biomolecules. A second energy charging time of the sensor module is determined, the second energy charging time representing the amount of time for the sensor to be completely charged by the transmitted RF energy, following mixing of the one or more probe biomolecules with one or more target biomolecule sample. A determination of whether biomolecule bonding has occurred is based on a variation of the first and second energy charging times.

13 Claims, 5 Drawing Sheets

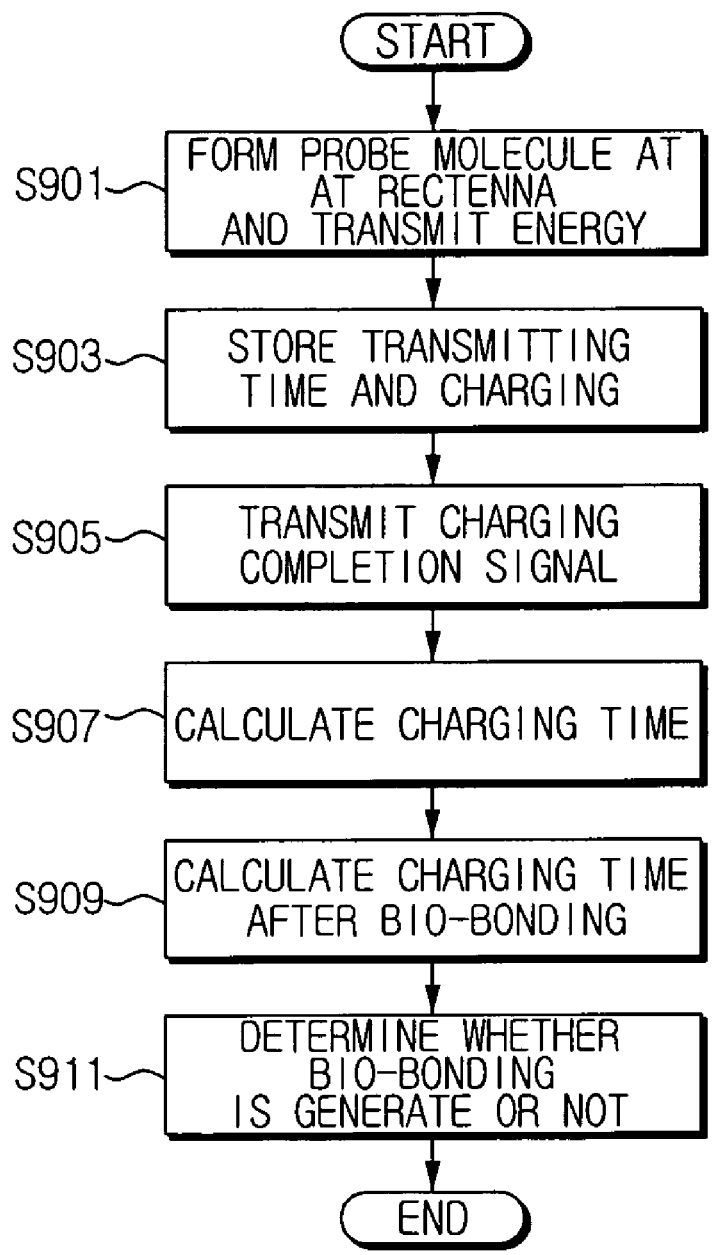

BIOMOLECULE BONDING DETECTION APPARATUS USING RF WIRELESS ENERGY TRANSMISSION AND METHOD THEREOF

This application claims priority to Korean Patent Application No. 2005-0002409 filed on Jan. 11, 2005 in the Korean Intellectual Property Office, and all the benefits accruing therefrom under 35 U.S.C. §119, and the disclosure of which is incorporated herein by reference.

BACKGROUND OF THE INVENTION

1. Field of the Invention

The present invention relates to an apparatus and method for detecting biomolecule bonding using radio frequency (RF) wireless energy transmission and a method thereof and, more particularly, to an apparatus and method for detecting biomolecule bonding by determining a time differential for charging a sensor module through transmission of RF wireless energy, wherein the charging time depends upon the extent of biomolecule bonding of probe biomolecules immobilized on the sensor module.

2. Description of the Related Art

A biomolecule chip is a biological microchip having biomolecules immobilized on a substrate. Biomolecule chips can be categorized based on the type of immobilized biomolecule, for example, DNA chips, protein chips, etc. A biomolecule which is immobilized on a chip and binds with a target biomolecule in a sample is called a probe. Biomolecule chip-related technical fields in development include, for example: biomolecule immobilization techniques for immobilizing biomolecules on a substrate, techniques for bonding immobilized biomolecules on a biomolecule chip with components of a sample, and biomolecule detection techniques for detecting the existence and the kind of biomolecules based on the analysis of a biomolecule chip where unknown biomolecules are immobilized.

Presently, there are several signal detection techniques in existence for the detection of biomolecule bonding. Broadly stated, these techniques may be classified into categories such as, for example, optical biomolecule bonding detection, chemical biomolecule bonding detection, mechanical biomolecule bonding detection, and electrical biomolecule detection, etc.

A conventional optical biomolecule bonding detection method is a method for optically determining whether a probe biomolecule is bonded to components of a sample. In order to detect the biomolecule bonding based on the optical biomolecule bonding detection method, biomolecule sample is labeled with a fluorescent material and is reacted with the probe biomolecule on the biomolecule chip such that ligands in the sample can bind with the probe biomolecule. The results of the reaction are then analyzed using a fluorescent detecting device so as to optically determine the amount of bonding with the probe biomaterials. However, the optical biomolecule bonding detecting method requires a pretreatment for mixing the fluorescent material with sample biomolecules before the sample is reacted with the probe. Therefore, the sample may be damaged or contaminated by the fluorescent material. A high-cost optical reader is also required for analyzing the result, and it is very complicated to analyze the result by using the optical reader. Furthermore, digitized data is not provided from the optical detection devices. Moreover, it is very difficult to miniaturize an optical detection apparatus.

Conventional mechanical biomolecule bonding detection methods detect a mechanical variation by utilizing an apparatus such as a cantilever, a surface acoustic wave (SAW) biosensor, or a scanning probe microscope (SPM). Where a cantilever is used, the biomolecule bonding is detected by measuring and comparing intermolecular cohesions before and after the probe biomolecule reacts with the sample biomolecule. In order to measure the intermolecular cohesion, the deflection of cantilever beam must be accurately measured. Therefore, the mechanical biomolecule bonding detection method requires supplementary equipment such as a laser.

Detection through a SAW biosensor utilizes the input of a signal at a predetermined frequency to a SAW filter, and the sample biomolecule reacts with the probe biomolecule on the SAW filter. The biomolecule bonding is detected by observing a filtering variation of the SAW filter generated by reaction of the sample biomolecule and the probe biomolecule. The mechanical biomolecule bonding detection method using the SAW requires additional equipment such as a laser device and a photo diode.

Conventional chemical biomolecule bonding detection methods detect the presence and absence of biomolecule bonding by analyzing the degree of electrochemical reaction of other chemical materials on an electrode on which probe biomolecules and sample biomolecules bind with each other. However, this method provides an inferior detection capability in comparison to optical biomolecule bonding detection methods.

In addition, conventional electrical biomolecule bonding detection methods may use structures such as, for example, a trench-type capacitance element or a planar-type capacitance element. However, since capacitance is proportional to cross sectional area and inversely proportional to thickness, it is difficult to design and form a capacitance element having an increased cross sectional area together while also ensuring efficient bio processing.

In particular, a detection method using a trench-type capacitor provides a method of reducing thickness and increasing cross sectional area of the capacitor by forming a deep trench, however it is not useful for bio processing since the resulting gap is very small. In contrast, a biomolecule bonding detection method using a capacitor in which a capacitance element is formed with a comb shape on a plane is disadvantageous in that only a relatively small number of capacitance elements are formed, since the metal film has a small thickness, and the detection sensitivity for biomolecules bonding is poor.

SUMMARY OF THE INVENTION

Accordingly, the present general inventive concept disclosed herein solves the above-mentioned disadvantages and/or problems, and an aspect of the present general inventive concept is to provide an apparatus for detecting a biomolecule bonding by determining a difference in the time for RF wireless charging of a sensor module, the rate of which is varied according to whether a biomolecule bonding has occurred with a probe biomolecule immobilized on a rectenna included in the sensor module.

In accordance with an aspect of the present invention, there is provided a biomolecule bonding detection method transmitting RF energy to a sensor module having one or more probe biomolecules immobilized thereon, and determining a first energy charging time of the sensor module, the first energy charging time representing the amount of time for the sensor to be completely charged by the transmitted RF energy, prior to mixing of the one or more probe biomolecules with one or more target sample biomolecules. A second energy charging time of the sensor module is determined, the second energy charging time representing the amount of time for the sensor to be completely charged by the transmitted RF energy, following mixing of the one or more probe biomolecules with one or more target biomolecule sample. A determination of whether biomolecule bonding has occurred is based on a variation of the first and second energy charging times.

In one embodiment, the RF energy transmitted to the sensor module is received by a rectifying antenna (rectenna) included therein, the RF energy rectified to a direct current and used as operating power for the sensor module. The RF energy is transmitted to the rectenna by an antenna included within a main body of a biomolecule bonding detection apparatus, the apparatus also including the sensor module.

The main body stores the time at which energy transmission to the sensor module begins, and the main body receives a charging completion signal sent by the sensor module when the sensor module is completely charged. The main body further records the time at which the charging completion signal is received.

The first and second energy charging times are calculated from respective energy transmission times and charge completion times.

In accordance with another aspect of the present invention, there is provided a biomolecule bonding detection apparatus comprising a sensor module including a rectifying antenna (rectenna) for receiving RF energy, the rectenna having one or more probe biomolecules immobilized thereon. A main body has an antenna for transmitting the RF energy to the rectenna, the main body configured to detect whether a biomolecule bonding has occurred by determining a difference in charging time of the sensor module by the transmitted RF energy before and after the one or more probe biomolecules are mixed with one or more target sample biomolecules.

The sensor module may include a generator for generating a charging completion signal when the sensor module is charged, wherein the rectenna is further configured to transmit a charging completion signal to the antenna in the main body, and a power supply for enabling the RF energy to be used as operating power for the sensor module.

The power supply may include a rectifier for rectifying the RF energy to a direct current.

The rectenna receives energy transmitting time information from the antenna, and transmits the received energy transmitting time information back to the antenna when the charging completion signal is transmitted to the antenna.

The antenna of the main body is configured for transmitting the energy to the rectenna and for receiving the charging completion signal from the rectenna. The main body further includes an analyzer for analyzing the difference in charging time of the sensor module by using the energy transmitting time information initially stored therein when the energy is first transmitted to the rectenna, and by using the time at which the charging completion signal is received from the rectenna.

Alternatively, the antenna of the main body is configured for transmitting both the RF energy and an energy transmitting time to the rectenna, and for receiving the charging completion signal from the rectenna, and for receiving the energy transmitting time information back from the rectenna. The main body further includes an analyzer for analyzing the difference in charging time of the sensor module by using the energy transmitting time from the rectenna, and by using the time at which the charging completion signal is received from the rectenna.

BRIEF DESCRIPTION OF THE DRAWINGS

The above aspects and features of the present invention will be more apparent by describing certain embodiments of the present invention with reference to the accompanying drawings, in which:

FIG. 3 is a flowchart of a method of detecting a biomolecule bonding using a RF wireless energy transmission in accordance with an embodiment of the present invention.

DETAILED DESCRIPTION OF THE INVENTION

Figure 1:
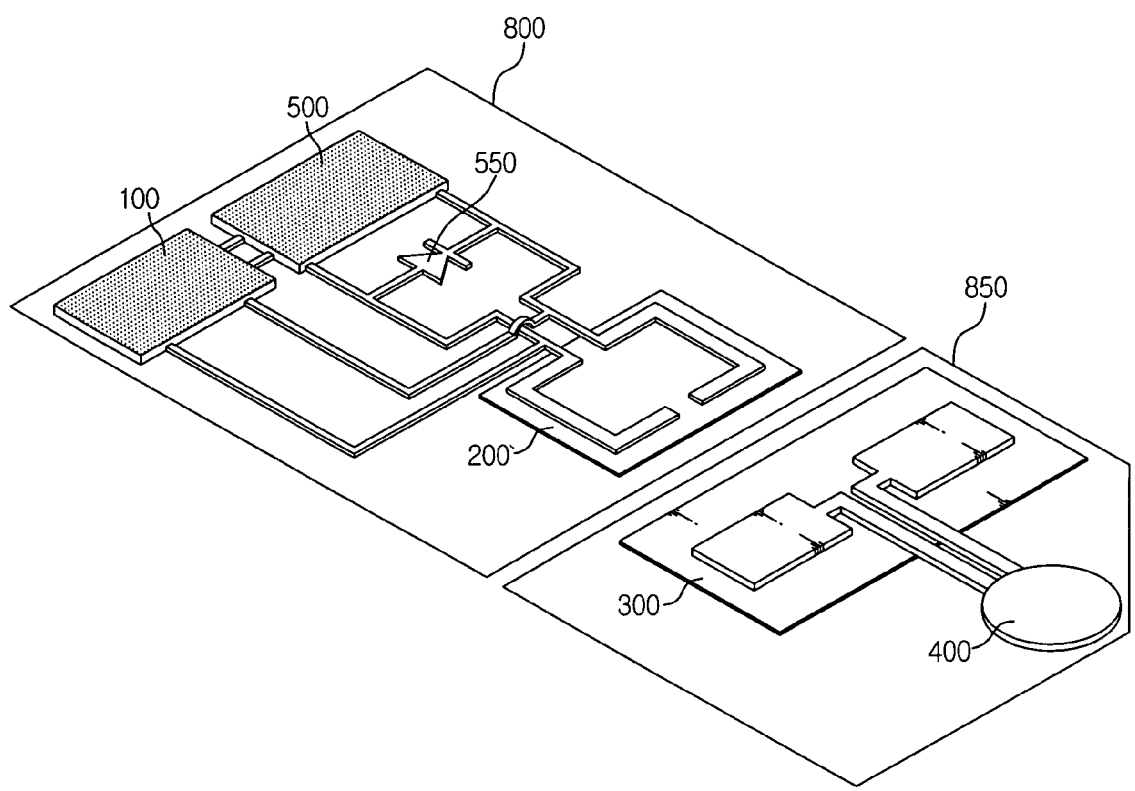
FIG. 1 is a perspective view of a biomolecule bonding detection apparatus using a RF wireless energy transmission in accordance with an embodiment of the present invention.

The invention is described more fully hereinafter with reference to the accompanying drawings, in which exemplary embodiments of the invention are shown. This invention may, however, be embodied in many different forms and should not be construed as limited to the exemplary embodiments set forth herein. Rather, these embodiments are provided so that this disclosure will be thorough and complete, and will fully convey the scope of the invention to those skilled in the art. In the drawings, the size and relative sizes of layers and regions may be exaggerated for clarity.

It will be understood that when an element or layer is referred to as being "on" or "connected to" another element or layer, the element or layer can be directly on or connected to another element or layer or intervening elements or layers. In contrast, when an element is referred to as being "directly on" or "directly connected to" another element or layer, there are no intervening elements or layers present. Like numbers refer to like elements throughout. As used herein, the term "and/or" includes any and all combinations of one or more of the associated listed items.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments of the invention are described herein with reference to schematic illustrations of idealized embodiments (and intermediate structures) of the invention. As such, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing. Also, well-known functions or constructions are not described in detail since they would obscure the invention in unnecessary detail.

FIG. 1 is a perspective view illustrating a biomolecule bonding detection apparatus using a radio frequency (RF) wireless energy transmission in accordance with an embodiment of the present invention.

Referring to FIG. 1, the biomolecule bonding detection apparatus includes a sensor module 800 having a rectenna (RECtifying anTENNA) 200 formed for transmitting/receiving energy, the rectenna 200 having probe biomolecules immobilized thereon, and a main body 850 configured for transmitting energy to the sensor module 800 and for analyzing the time for charging a power supply in the sensor module 800. Hereinafter, the time for charging the power supply in the sensor module 800 is referred to as the energy charging time. The sensor module 800 includes a generator 100, the rectenna 200 and a power supply 500 having a rectifier 550. The main body 850 includes an antenna 300 and an analyzer 400. As is known in the art, a "rectenna" is an antenna comprising a mesh of dipoles and diodes that receives RF energy (e.g., microwaves) a transmitter and converts the same into direct current.

The antenna 300 transmits energy generated by the analyzer 400 from the main body 850 to the sensor module 800. In order to measure the energy charging time, the main body 850 stores the time at which the transmission of the generated energy begins or, alternatively, transmits the time information to the sensor module 800 along with the charging energy itself.

In either case, the rectenna 200 receives the energy transmitted from the antenna 300, with at least one probe biomolecule formed on the rectenna 200. As described above, the probe biomolecule is used for searching target generic information in a sample. The rectenna 200 may also receive the energy transmitting time information from the main body 850 through the antenna 300. In this case the rectenna 200 will transmit the received energy transmitting time information back to the main body 850 once the sensor module 800 is charged.

The power supply 500 enables the energy received by the rectenna 200 to be used as operating power for the sensor module 800. The power supply 500 includes the rectifier 550 for rectifying the received RF energy transmitted from the antenna 300 to a direct current. The power supply 500, in turn, transfers the generated power to the generator 100 and back to the rectenna 200. In the exemplary embodiment depicted, the rectifier 500 is included in the power supply 500. However, the rectifier 500 may also be included in the rectenna 200.

The generator 100 generates a charging completion signal when the received energy transmitted from the antenna 300 has completely charged the sensor module 800. The generated charging completion signal is transmitted back to the antenna 300 of the main body 850 through the rectenna 200. Again, if the rectenna 200 initially receives the energy transmitting time information from the antenna 300 when the energy is first transmitted, the rectenna 200 also transmits the time information back to the antenna 300, along with the charging completion signal.

In addition to generating energy to be transmitted to the sensor module 800, the analyzer 400 also analyzes the energy charging time, which is the total time taken to charge the sensor module 800. Thereby, the analyzer 400 may determine whether biomolecule bonding has occurred.

More specifically, the analyzer 400 calculates the energy charging time by comparing the initial energy transmission time with the time the charging completion signal sent from the rectenna 200 to the antenna 300 was received. Thus, the difference between the energy transmitting time and the charging completion signal time represents the energy charging time.

As described above, the analyzer 400 may either store the energy transmitting time information when the energy is first transmitted to the sensor module 800, or transmits the energy transmitting time information along with the energy to the sensor module 800. Accordingly, the analyzer 400 will either use the energy transmitting time information stored in the analyzer 400, or receive the energy transmitting time information from the sensor module 800.

Furthermore, the analyzer 400 calculates a first energy charging time before the probe biomolecule is mixed with a target sample, and stores the first energy charging time. The analyzer 400 also calculates a second energy charging time after the probe biomolecule is mixed with the target sample, and stores the second calculated energy charging time. The analyzer 400 then compares the first energy charging time and the second energy charging time. If there is a difference between the first energy charging time and the second energy charging time, the analyzer 400 determines that the biomolecule bonding has occurred.

Figure 2A:
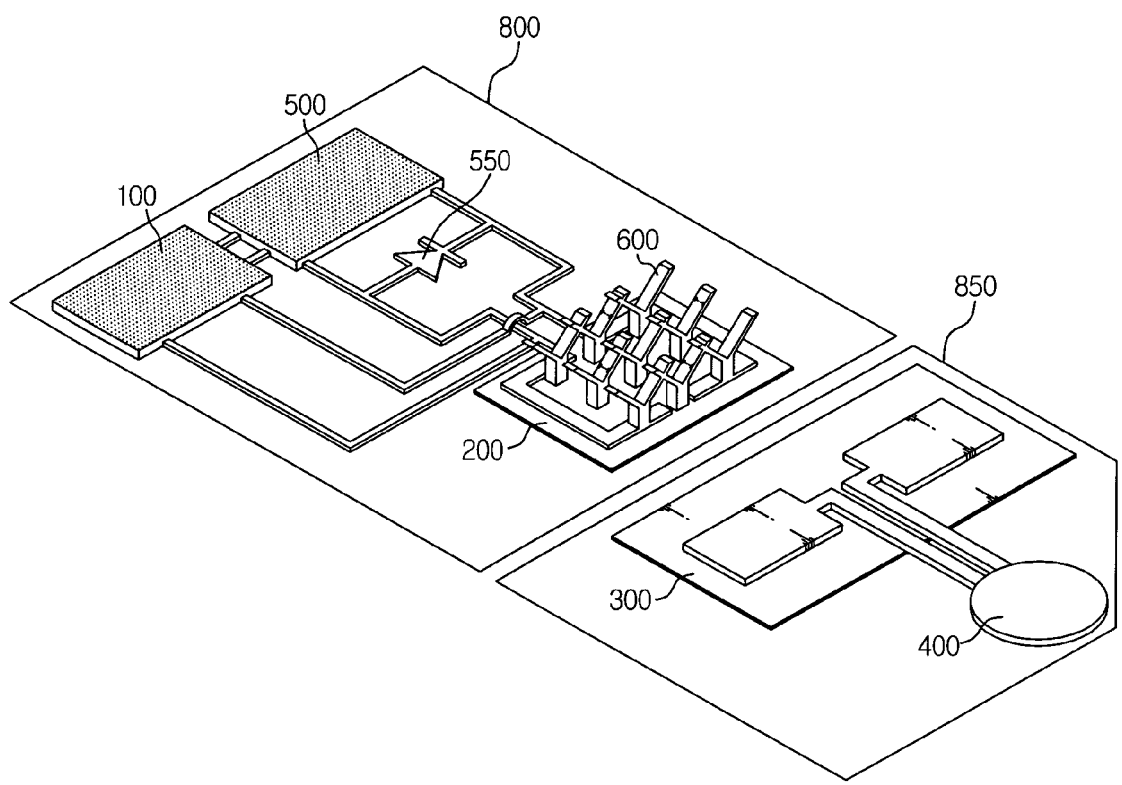
FIGS. 2A to 2C perspective views illustrating a method of detecting a biomolecule bonding using the biomolecule bonding detection apparatus shown in FIG. 1.
Figure 2B:
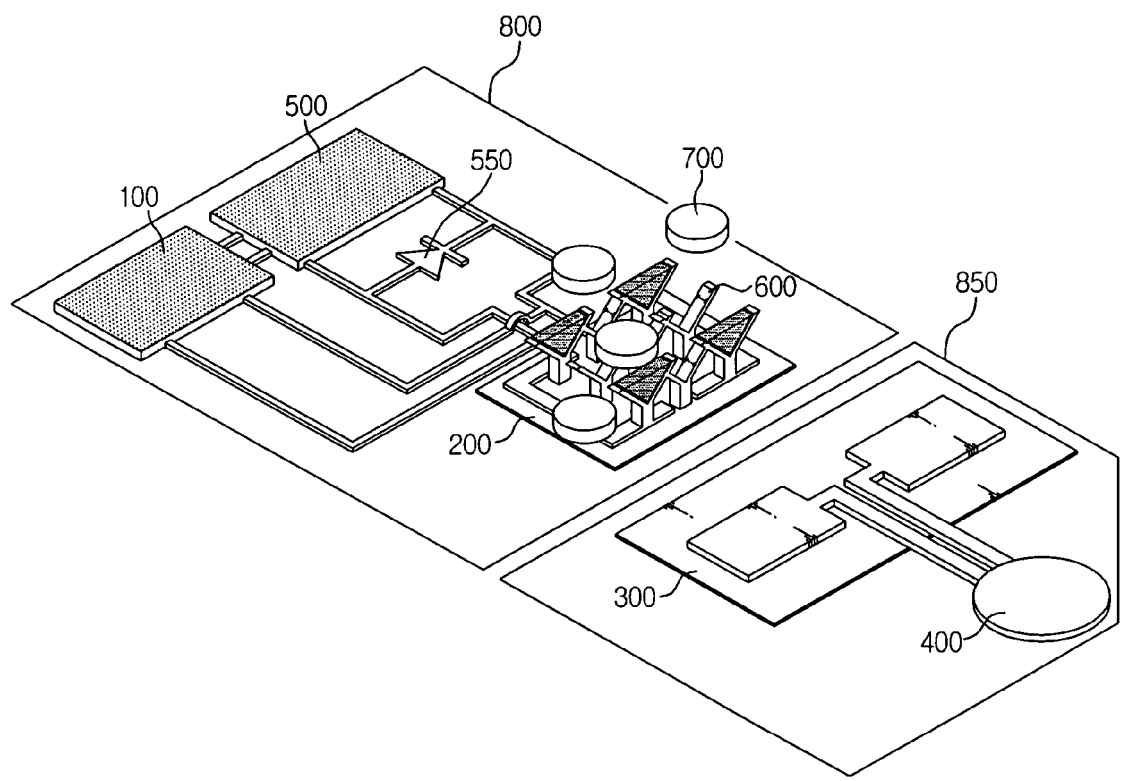
Figure 2C:
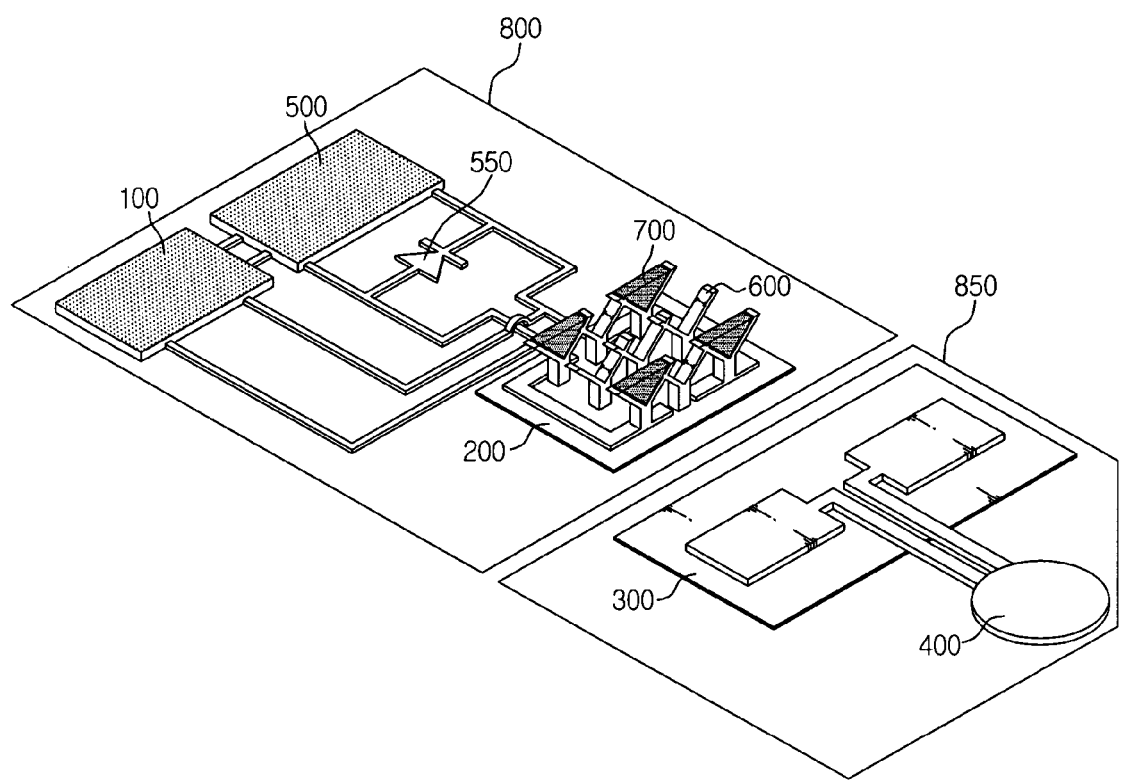

FIGS. 2A to 2C perspective views of a biomolecule bonding detection apparatus for illustrating a method of detecting a biomolecule bonding using the biomolecule bonding detection apparatus shown in FIG. 1. FIG. 2A schematically illustrates a biomolecule bonding detection apparatus in which a probe biomolecule 600 is immobilized on the rectenna 200. FIG. 2B shows the biomolecule bonding detection apparatus after a target sample biomolecule 700 has been mixed with and biologically bonded to a probe biomolecule 600 formed on the rectenna 200. FIG. 2C shows the biomolecule bonding detection apparatus when any of the target sample biomolecules 700 not biologically bonded to a corresponding probe biomolecule 600 are cleaned (removed).

Referring to FIG. 2A, a probe biomolecule 600 is immobilized on the rectenna 200 of the sensor module 800 in order to detect the biomolecule bonding. After immobilization of the probe biomolecule 600, an energy charging time is calculated. That is, the main body 850 initially transmits energy to the rectenna 200 of the sensor module 800 prior to any bonding of the probe biomolecules with any of the target sample biomolecules. The analyzer 400 calculates a first time for charging the sensor module 800 by the energy transmitted from the main body 850. The transmitted energy to the rectenna 200 is used as operational power for the sensor module 800 by the power supply 500 and the rectifier 550.

Referring to FIG. 2B, one or more target sample biomolecules 700 are biologically bonded to one or more corresponding probe biomolecules 600 immobilized on the rectenna 200. In addition, any the target sample biomolecules 700 not bonded are removed.

Referring to FIG. 2C, a second energy charging time is calculated by again by transmitting energy from the main body 850 to the sensor module 800. Then, the first energy charging time is compared to the second energy charging time. If there is a difference between the first energy charging time and the second energy charging time as a result of the comparison, the analyzer 400 determines that the biomolecule bonding has occurred.

FIG. 3 is a flowchart of a method of detecting a biomolecule bonding using a RF wireless energy transmission, in accordance with an embodiment of the present invention. In order to perform the biomolecule bonding detection method, a biomolecule bonding detection apparatus similar to that shown in FIG. 1 is used. As described above, the biomolecule bonding detection apparatus includes the sensor module 800 and rectenna 200 on which the probe biomolecule is immobilized, and the main body 850 having the antenna 300 transmitting energy to the sensor module 800.

Referring to FIG. 3, the probe biomolecule 600 is immobilized on the rectenna 200 (configured for transmitting/receiving wireless energy), and the analyzer 400 generates and transmits the energy to the rectenna 200 of the sensor module 800 through the antenna 300 in operation S901.

The analyzer 400 stores the energy transmitting time information representing the time energy from the analyzer 400 is first transmitted to the sensor module 800 in order to calculate a first energy charging time in operation S903. The energy transmitting time information may alternatively be transmitted to the rectenna 200 along with the generated energy. In this case, the energy transmitting time information is re-transmitted from the sensor module 800 back to the analyzer 400 so the analyzer 400 may calculate the first energy charging time.

Once the sensor module 800 is completely charged from energy transmitted from the main body 850, a charging completion signal is generated and transmitted back to the main body 850 (received by the antenna 300) in operation S905. After complete charging of the sensor module 800, the received energy is used as operating power of the sensor module 800 by the power supply 500, while the generator 100 generates the charging completion signal. The charging completion signal is transmitted to the antenna 300 through the rectenna 200.

Where the rectenna 200 receives the energy transmitting time information from the main body 850 along with the energy is transmitted from the main body 850 to the sensor module 800, this energy transmitting time information is also re-transmitted back to the antenna 300 with the charging completion signal.

Once the analyzer 400 receives the charging completion signal, the analyzer 400 then determines a signal receiving time corresponding to the time the charging completion signal was received, and thereafter calculates a first energy charging time, in operation S907. The first energy charging time is calculated by obtaining the difference between the energy transmitting time and the signal receiving time. As described above, the analyzer 400 uses the energy transmitting time information initially stored in the analyzer 400 or alternatively receives the energy transmitting time information back from the sensor module 800. By receiving the energy transmitting time information from the sensor module 800, energy charging times for a plurality of sensor modules can be calculated. That is, the analyzer 400 can calculate the energy charging times of a plurality of sensor modules by receiving the energy transmitting time information from the plurality of sensor modules.

By exchanging the energy transmitting time information between the sensor module 800 and the main body 850 after storing the energy transmitting time information in the main body 850, it is possible to determine whether the energy is received or transmitted between the sensor module 800 and the main body 850.

After calculating the first energy charging time, the probe biomolecule 600 is mixed with and biologically bonded to the target sample biomolecule 700, with any of the target sample biomolecules 700 not bonded to the probe biomolecule 600 being cleaned, and a second energy charging time of the sensor module 800 is calculated in operation S909.

After calculating the second energy charging time, the second energy charging time is compared to the first energy charging time. If there is a difference between the second energy charging time and the first energy charging time, the analyzer 400 determines that biomolecule bonding has occurred, as shown in operation S911.

As described above, the biomolecule bonding detection apparatus and method thereof conveniently detects the biomolecule bonding by transmitting energy from the main body to the rectenna of the sensor module, and calculating the difference of the energy charging time, which may vary depending on whether the probe biomolecule has biologically bonded to the target sample biomolecule.

As will also be appreciated, the biomolecule bonding detection apparatus according to the present invention may be implemented as simple structured device.

The foregoing embodiment and advantages are merely exemplary and are not to be construed as limiting the present invention. The present teaching can be readily applied to other types of apparatuses. Also, the description of the embodiments of the present invention is intended to be illustrative, and not to limit the scope of the claims, and many alternatives, modifications, and variations will be apparent to those skilled in the art.

What is claimed is:

1. A biomolecule bonding detection method, comprising:
   transmitting RF energy to a sensor module having one or more probe biomolecules immobilized thereon;
   determining a first energy charging time of the sensor module, the first energy charging time representing the amount of time for the sensor module to be completely charged by the transmitted RF energy, prior to mixing of the one or more probe biomolecules with one or more target sample biomolecules;
   determining a second energy charging time of the sensor, the second energy charging time representing the amount of time for the sensor to be completely charged by the transmitted RF energy, following mixing of the one or more probe biomolecules with one or more target biomolecule sample; and
   determining whether biomolecule bonding has occurred based on a variation of the first and second energy charging times.

2. The biomolecule bonding detection method of claim 1, wherein the RF energy transmitted to the sensor module is received by a rectifying antenna (rectenna) included therein, the RF energy rectified to a direct current and used as operating power for the sensor module.

3. The biomolecule bonding detection method of claim 2, wherein the RF energy is transmitted to the rectenna by an antenna included within a main body of a biomolecule bonding detection apparatus, the apparatus also including the sensor module.

4. The biomolecule bonding detection method of claim 2, wherein the main body stores the time at which energy transmission to the sensor module begins, and wherein the main body receives a charging completion signal sent by the sensor module when the sensor module is completely charged, the main body further recording the time at which the charging completion signal is received.

5. The biomolecule bonding detection method of claim 4, wherein the first and second energy charging times are calculated from respective energy transmission times and charge completion times.

6. The biomolecule bonding detection method of claim 2, wherein the main body transmits, along with the RF energy, the time at which energy transmission to the sensor module begins, and wherein the main body receives the energy transmission time back from the sensor module, along with a charging completion signal sent by the sensor module when the sensor module is completely charged, the main body further recording the time at which the charging completion signal is received.

7. The biomolecule bonding detection method of claim 6, wherein the first and second energy charging times are calculated from respective energy transmission times and charge completion times.

8. A biomolecule bonding detection apparatus comprising:
a sensor module including a rectifying antenna for receiving radio frequency energy, the rectifying antenna having one or more probe biomolecules immobilized thereon; and
a main body having an antenna for transmitting the radio frequency energy to the rectifying antenna, the main body configured to detect whether a biomolecule bonding has occurred by determining a difference in charging time of the sensor module by the transmitted radio frequency energy before and after the one or more probe biomolecules are mixed with one or more target sample biomolecules.

9. The biomolecule bonding detection apparatus of claim 8, wherein the sensor module includes:
a generator for generating a charging completion signal when the sensor module is charged, wherein the rectifying antenna is further configured to transmit the charging completion signal to the antenna in the main body; and
a power supply for enabling the radio frequency energy to be used as operating power for the sensor module.

10. The biomolecule bonding detection apparatus of claim 9, wherein the power supply includes a rectifier for rectifying the radio frequency energy to a direct current.

11. The biomolecule bonding detection apparatus of claim 9, wherein the rectifying antenna receives energy transmitting time information from the antenna, and transmits the received energy transmitting time information back to the antenna when the charging completion signal is transmitted to the antenna.

12. The biomolecule bonding detection apparatus of claim 9, wherein:
the antenna of the main body is configured for transmitting the energy to the rectifying antenna and for receiving the charging completion signal from the rectifying antenna; and
the main body further includes an analyzer for analyzing the difference in charging time of the sensor module by using the energy transmitting time information initially stored therein when the energy is first transmitted to the rectifying antenna, and by using the time at which the charging completion signal is received from the rectifying antenna.

13. The biomolecule bonding detection apparatus of claim 9, wherein:
the antenna of the main body is configured for transmitting both the radio frequency energy and an energy transmitting time to the rectifying antenna, and for receiving the charging completion signal from the rectifying antenna, and for receiving the energy transmitting time information back from the rectifying antenna; and
the main body further includes an analyzer for analyzing the difference in charging time of the sensor module by using the energy transmitting time from the rectifying antenna, and by using the time at which the charging completion signal is received from the rectifying antenna.

* * * * *